United States Patent
He et al.

(10) Patent No.: US 12,297,255 B2
(45) Date of Patent: May 13, 2025

(54) ENGINEERED PICHIA STRAIN AND A RECOMBINANT METHOD OF USING THE SAME FOR MAKING A COLLAGEN SPONGE

(71) Applicant: Shaanxi Huikang Bio-Tech Co., Ltd., Xi'an (CN)

(72) Inventors: Yue He, Xi'an (CN); Jiuna Wang, Xi'an (CN); Jinli Zhao, Xi'an (CN)

(73) Assignee: Shaanxi Huikang Bio-Tech Co., Ltd., Xi'an (CN)

( * ) Notice: Subject to any disclaimer, the term of this patent is extended or adjusted under 35 U.S.C. 154(b) by 792 days.

(21) Appl. No.: 17/367,212

(22) Filed: Jul. 2, 2021

(65) Prior Publication Data

US 2021/0363226 A1 Nov. 25, 2021

Related U.S. Application Data

(63) Continuation of application No. PCT/CN2020/108308, filed on Aug. 11, 2020.

(30) Foreign Application Priority Data

Jan. 17, 2020 (CN) .......................... 202010052422.9

(51) Int. Cl.
| | | |
|---|---|---|
| C07K 14/78 | (2006.01) | |
| A61L 15/32 | (2006.01) | |
| A61L 15/42 | (2006.01) | |
| C08J 9/28 | (2006.01) | |
| C08J 9/36 | (2006.01) | |
| C12N 1/14 | (2006.01) | |
| C12R 1/84 | (2006.01) | |

(52) U.S. Cl.
CPC ............ *C07K 14/78* (2013.01); *A61L 15/325* (2013.01); *A61L 15/425* (2013.01); *C08J 9/28* (2013.01); *C08J 9/36* (2013.01); *C12N 1/145* (2021.05); *A61L 2300/418* (2013.01); *A61L 2400/04* (2013.01); *C08J 2201/0484* (2013.01); *C08J 2389/00* (2013.01); *C12R 2001/84* (2021.05)

(58) Field of Classification Search
CPC ....... C07K 14/78; C12N 1/145; A61L 15/325; A61L 15/425; A61L 2300/418; A61L 2400/04; C08J 9/28; C08J 9/36; C08J 2201/0484; C08J 2389/00; C12R 2001/84
See application file for complete search history.

(56) References Cited

U.S. PATENT DOCUMENTS 6,541,023 B1 * 4/2003 Andre et al. .......... A61L 27/3891

FOREIGN PATENT DOCUMENTS

| CN | 101890179 A | 11/2010 |
|---|---|---|
| CN | 103432620 A | 12/2013 |
| CN | 104558675 A | 4/2015 |
| CN | 108070032 | * 5/2018 |
| CN | 108070032 A | 5/2018 |
| CN | 109608551 A | 4/2019 |
| CN | 110256572 A | 9/2019 |
| CN | 111187347 A | 5/2020 |

OTHER PUBLICATIONS

Wang et al., Production of recombinant collagen: state of the art and challenges, 2017, Engineering Biology, 1(1): 18-23 (Year: 2017).*
Zhang et al. A novel strategy to fabricate water-soluble collagen using poly(γ-glutamic acid)-derivatives as dual-functional modifier, 2018, Reactive and Functional Polymers, 122: 131-139 (Year: 2018).*
Schoof et al. Control of Pore Structure and Size in Freeze-Dried Collagen Sponges, 2001, Journal of Biomedical Materials Research, 2001, 58(4): 352-357) (Year: 2001).*
Bax et al. Fundamental insight into the effect of carbodiimide crosslinking on cellular recognition of collagen-based scaffolds, 2017, Acta Biomateralia, 2017, 218-234 (Year: 2017).*
Peng et al. Stabilisation of Collagen Sponges by Glutaraldehyde Vapour Crosslinking, 2017, International Journal of Biomaterials, 2017, pp. 1-6 (Year: 2017).*
First Office Action issued on Nov. 19, 2021 for counterpart Australian patent application No. 2020403707.
Chen, Z., et al., "Exploring the Potential of the Recombinant Human Collagens for Biomedical and Clinical Applications: a Short Review," Biomedical materials, Institute of Physics Publishing, Bristol, GB, Dec. 12, 2020, vol. 16(1), pp. 12001, XP020362361.
Extended European Search Report dated Aug. 25, 2022 in Application No. EP20900719.4.
He, Y., et al., "A Novel Gene Recombinant Collagen Hemostatic Sponge With Excellent Biocompatibility and Hemostatic Effect," International journal of biological macromolecules, May 1, 2021, vol. 178, pp. 296-305.
Liu, B., et al., "Structure Analysis of a Highly Hydrophilic Recombinant Human-Source Gelatin," Chemical Science Transactions, Jan. 1, 2012, vol. 1(2), pp. 347-354, XP55951098.

(Continued)

*Primary Examiner* — Hope A Robinson
(74) *Attorney, Agent, or Firm* — Weaver Austin Villeneuve & Sampson LLP (57) ABSTRACT

The present disclosure provides a recombinant collagen and a recombinant collagen sponge material. The recombinant collagen comprises: (a) a protein composed of the amino acid sequence represented by SEQ ID NO: 2; and/or (b) a protein which has the same function as (a) and is derived from (a) by substitution, deletion and/or addition of one or more amino acids in SEQ ID NO:2. The recombinant collagen sponge material is obtained by sequential physical cross-linking and chemical cross-linking of the recombinant collagen. The recombinant collagen sponge material according to the present disclosure is capable of hemostasis, wound surface repair, moisture absorption and platelet aggregation, and has high moisture absorption, a significant hemostatic effect and good biocompatibility, assuming great clinical significance in the field of surgery.

17 Claims, 8 Drawing Sheets

Specification includes a Sequence Listing.

(56) References Cited

OTHER PUBLICATIONS

Hou zengmiao, Preparation and characterization of recombinant human-source collagen, Chinese Journal of Biotechnology, vol. 35 No.2.

GenBank:MH544244.1 Synthetic construct collagen-like protein gene, partial cds, Sep. 25, 2018.

He yue, preparation and properties of recombinant collagen sponge, vol. 23, No. 6.

Xinhua Liu, Recent advances of collagen-based biomaterials: Multi-hierarchical structure, modification and biomedical applications, Materials Science & Engineering C, vol. 99.

International search report (English Translation) issued for International application No. PCT/CN2020/108308 mailed on Nov. 17, 2020.

* cited by examiner

SEQUENCE LISTING

<160> NUMBER OF SEQ ID NOS: 3

<210> SEQ ID NO 1
<211> LENGTH: 1233
<212> TYPE: DNA
<213> ORGANISM: Artificial Sequence
<220> FEATURE:
<223> OTHER INFORMATION: Recombinant collagen polynucleotide
<220> FEATURE:
<221> NAME/KEY: CDS
<222> LOCATION: (1)..(1233)

<400> SEQUENCE: 1

```
ggt cct ccc ggc gaa cca ggt aat cct ggt aaa cct ggt tct ccc ggc      48
Gly Pro Pro Gly Glu Pro Gly Asn Pro Gly Lys Pro Gly Ser Pro Gly
1               5                   10                  15 cca gct ggt tcc aac ggg gag ccg ggt cct gcc ggc tca ccc gga gaa      96
Pro Ala Gly Ser Asn Gly Glu Pro Gly Pro Ala Gly Ser Pro Gly Glu
            20                  25                  30 aag ggg tcg caa ggt agt aat ggc aac cca gga ccg gca ggg aat cag     144
Lys Gly Ser Gln Gly Ser Asn Gly Asn Pro Gly Pro Ala Gly Asn Gln
        35                  40                  45 ggt caa cct ggc aac aaa gga agc ccc ggg aat cca ggt aag ccg ggc     192
Gly Gln Pro Gly Asn Lys Gly Ser Pro Gly Asn Pro Gly Lys Pro Gly
    50                  55                  60 gag cct gga tct aac ggg ccc cag ggt gaa cca ggc tcc caa gga aat     240
Glu Pro Gly Ser Asn Gly Pro Gln Gly Glu Pro Gly Ser Gln Gly Asn
65                  70                  75                  80 ccg ggg aaa aac ggt cag cct ggc tca ccc gga tcg caa ggg agt cca     288
Pro Gly Lys Asn Gly Gln Pro Gly Ser Pro Gly Ser Gln Gly Ser Pro
                85                  90                  95 ggt aat cag ggc caa ccg gga aag cct ggg cag ccc ggt gag caa ggc     336
Gly Asn Gln Gly Gln Pro Gly Lys Pro Gly Gln Pro Gly Glu Gln Gly
            100                 105                 110 agc cca gga aac cag ggg ccg gcg ggt aat gaa ggc cct aaa gga caa     384
Ser Pro Gly Asn Gln Gly Pro Ala Gly Asn Glu Gly Pro Lys Gly Gln
        115                 120                 125 ccc ggg cag aac ggt aag cca gga tcc ccg ggt cct ccc ggc gaa cca     432
Pro Gly Gln Asn Gly Lys Pro Gly Ser Pro Gly Pro Pro Gly Glu Pro
    130                 135                 140 ggt aat cct ggt aaa cct ggt tct ccc ggc cca gct ggt tcc aac ggg     480
Gly Asn Pro Gly Lys Pro Gly Ser Pro Gly Pro Ala Gly Ser Asn Gly
145                 150                 155                 160
```

```
gag ccg ggt cct gcc ggc tca ccc gga gaa aag ggg tcg caa ggt agt    528
Glu Pro Gly Pro Ala Gly Ser Pro Gly Glu Lys Gly Ser Gln Gly Ser
            165                 170                 175 aat ggc aac cca gga ccg gca ggg aat cag ggt caa cct ggc aac aaa    576
Asn Gly Asn Pro Gly Pro Ala Gly Asn Gln Gly Gln Pro Gly Asn Lys
            180                 185                 190 gga agc ccc ggg aat cca ggt aag ccg ggc gag cct gga tct aac ggg    624
Gly Ser Pro Gly Asn Pro Gly Lys Pro Gly Glu Pro Gly Ser Asn Gly
            195                 200                 205 ccc cag ggt gaa cca ggc tcc caa gga aat ccg ggg aaa aac ggt cag    672
Pro Gln Gly Glu Pro Gly Ser Gln Gly Asn Pro Gly Lys Asn Gly Gln
            210                 215                 220 cct ggc tca ccc gga tcg caa ggg agt cca ggt aat cag ggc caa ccg    720
Pro Gly Ser Pro Gly Ser Gln Gly Ser Pro Gly Asn Gln Gly Gln Pro
225                 230                 235                 240 gga aag cct ggg cag ccc ggt gag caa ggc agc cca gga aac cag ggg    768
Gly Lys Pro Gly Gln Pro Gly Glu Gln Gly Ser Pro Gly Asn Gln Gly
            245                 250                 255 ccg gcg ggt aat gaa ggc cct aaa gga caa ccc ggg cag aac ggt aag    816
Pro Ala Gly Asn Glu Gly Pro Lys Gly Gln Pro Gly Gln Asn Gly Lys
            260                 265                 270 cca ggt acc cca ggt cct ccc ggc gaa cca ggt aat cct ggt aaa cct    864
Pro Gly Thr Pro Gly Pro Pro Gly Glu Pro Gly Asn Pro Gly Lys Pro
            275                 280                 285 ggt tct ccc ggc cca gct ggt tcc aac ggg gag ccg ggt cct gcc ggc    912
Gly Ser Pro Gly Pro Ala Gly Ser Asn Gly Glu Pro Gly Pro Ala Gly
            290                 295                 300 tca ccc gga gaa aag ggg tcg caa ggt agt aat ggc aac cca gga ccg    960
Ser Pro Gly Glu Lys Gly Ser Gln Gly Ser Asn Gly Asn Pro Gly Pro
305                 310                 315                 320 gca ggg aat cag ggt caa cct ggc aac aaa gga agc ccc ggg aat cca   1008
Ala Gly Asn Gln Gly Gln Pro Gly Asn Lys Gly Ser Pro Gly Asn Pro
            325                 330                 335 ggt aag ccg ggc gag cct gga tct aac ggg ccc cag ggt gaa cca ggc   1056
Gly Lys Pro Gly Glu Pro Gly Ser Asn Gly Pro Gln Gly Glu Pro Gly
            340                 345                 350 tcc caa gga aat ccg ggg aaa aac ggt cag cct ggc tca ccc gga tcg   1104
Ser Gln Gly Asn Pro Gly Lys Asn Gly Gln Pro Gly Ser Pro Gly Ser
            355                 360                 365 caa ggg agt cca ggt aat cag ggc caa ccg gga aag cct ggg cag ccc   1152
Gln Gly Ser Pro Gly Asn Gln Gly Gln Pro Gly Lys Pro Gly Gln Pro
            370                 375                 380 ggt gag caa ggc agc cca gga aac cag ggg ccg gcg ggt aat gaa ggc   1200
Gly Glu Gln Gly Ser Pro Gly Asn Gln Gly Pro Ala Gly Asn Glu Gly
385                 390                 395                 400 cct aaa gga caa ccc ggg cag aac ggt aag cca                       1233
Pro Lys Gly Gln Pro Gly Gln Asn Gly Lys Pro
            405                 410
```

<210> SEQ ID NO 2
<211> LENGTH: 411
<212> TYPE: PRT
<213> ORGANISM: Artificial Sequence
<220> FEATURE:
<223> OTHER INFORMATION: Synthetic Construct

<400> SEQUENCE: 2

```
Gly Pro Pro Gly Glu Pro Gly Asn Pro Gly Lys Pro Gly Ser Pro Gly
1               5                   10                  15

Pro Ala Gly Ser Asn Gly Glu Pro Gly Pro Ala Gly Ser Pro Gly Glu
```

20                  25                  30
Lys Gly Ser Gln Gly Ser Asn Gly Asn Pro Gly Pro Ala Gly Asn Gln
                35                  40                  45

Gly Gln Pro Gly Asn Lys Gly Ser Pro Gly Asn Pro Gly Lys Pro Gly
        50                  55                  60

Glu Pro Gly Ser Asn Gly Pro Gln Gly Glu Pro Gly Ser Gln Gly Asn
 65                  70                  75                  80

Pro Gly Lys Asn Gly Gln Pro Gly Ser Pro Gly Ser Gln Gly Ser Pro
                85                  90                  95

Gly Asn Gln Gly Gln Pro Gly Lys Pro Gly Gln Pro Gly Glu Gln Gly
                100                 105                 110

Ser Pro Gly Asn Gln Gly Pro Ala Gly Asn Glu Gly Pro Lys Gly Gln
                115                 120                 125

Pro Gly Gln Asn Gly Lys Pro Gly Ser Pro Gly Pro Gly Glu Pro
                130                 135                 140

Gly Asn Pro Gly Lys Pro Gly Ser Pro Gly Pro Ala Gly Ser Asn Gly
145                 150                 155                 160

Glu Pro Gly Pro Ala Gly Ser Pro Gly Glu Lys Gly Ser Gln Gly Ser
                165                 170                 175

Asn Gly Asn Pro Gly Pro Ala Gly Asn Gln Gly Gln Pro Gly Asn Lys
                180                 185                 190

Gly Ser Pro Gly Asn Pro Gly Lys Pro Gly Glu Pro Gly Ser Asn Gly
                195                 200                 205

Pro Gln Gly Glu Pro Gly Ser Gln Gly Asn Pro Gly Lys Asn Gly Gln
                210                 215                 220

Pro Gly Ser Pro Gly Ser Gln Gly Ser Pro Gly Asn Gln Gly Gln Pro
225                 230                 235                 240

Gly Lys Pro Gly Gln Pro Gly Glu Gln Gly Ser Pro Gly Asn Gln Gly
                245                 250                 255

Pro Ala Gly Asn Glu Gly Pro Lys Gly Gln Pro Gly Gln Asn Gly Lys
                260                 265                 270

Pro Gly Thr Pro Gly Pro Gly Glu Pro Gly Asn Pro Gly Lys Pro
                275                 280                 285

Gly Ser Pro Gly Pro Ala Gly Ser Asn Gly Glu Pro Gly Pro Ala Gly
                290                 295                 300

Ser Pro Gly Glu Lys Gly Ser Gln Gly Ser Asn Gly Asn Pro Gly Pro
305                 310                 315                 320

Ala Gly Asn Gln Gly Gln Pro Gly Asn Lys Gly Ser Pro Gly Asn Pro
                325                 330                 335

Gly Lys Pro Gly Glu Pro Gly Ser Asn Gly Pro Gln Gly Glu Pro Gly
                340                 345                 350

Ser Gln Gly Asn Pro Gly Lys Asn Gly Gln Pro Gly Ser Pro Gly Ser
                355                 360                 365

Gln Gly Ser Pro Gly Asn Gln Gly Gln Pro Gly Lys Pro Gly Gln Pro
                370                 375                 380

Gly Glu Gln Gly Ser Pro Gly Asn Gln Gly Pro Ala Gly Asn Glu Gly
385                 390                 395                 400

Pro Lys Gly Gln Pro Gly Gln Asn Gly Lys Pro
                405                 410

<210> SEQ ID NO 3
<211> LENGTH: 15
<212> TYPE: PRT
<213> ORGANISM: Artificial Sequence

```
<220> FEATURE:
<223> OTHER INFORMATION: For recombinant collagen validation

<400> SEQUENCE: 3

Gly Pro Pro Gly Glu Pro Gly Asn Pro Gly Lys Pro Gly Ser Pro
1               5                   10                  15
```

ENGINEERED PICHIA STRAIN AND A RECOMBINANT METHOD OF USING THE SAME FOR MAKING A COLLAGEN SPONGE

CROSS-REFERENCE TO RELATED APPLICATIONS

An Application Data Sheet is filed concurrently with this specification as part of the present application. Each application that the present application claims benefit of or priority to as identified in the concurrently filed Application Data Sheet is incorporated by reference herein in its entirety and for all purposes.

SEQUENCE LISTING

The instant application contains a Sequence Listing which is submitted electronically in ASCII format and is hereby incorporated by reference in its entirety. Said ASCII copy, created on Jul. 1, 2021, is named SANYP012_Sequence_Listing.txt and is 10 KB in size.

TECHNICAL FIELD

The present disclosure relates to the technical field of medical technology and surgery, particularly relates to a recombinant collagen, a recombinant collagen sponge material, a method for preparation thereof, and use thereof, and more particularly to a recombinant collagen sponge material capable of hemostasis and wound surface repair, a method for preparation thereof, and use thereof.

BACKGROUND

In our daily lives there are many scenarios where uncontrolled bleeding is the main cause of sudden accidents and massive bleeding in medical operations, such as first-aid treatment for emergencies and hemostasis in trauma during surgery, and thus effective and rapid local hemostasis for patients is of particular importance. Therefore, shortening the hemostasis time of hemostatic materials and improving the quality of hemostasis has become an optimal strategy to reduce mortality among patients. Clinically commonly used hemostatic materials, such as cellulose-based hemostatic gauze, hemostatic fibers, and hemostatic bandages, have limitations in use, for example long hemostasis time, inability to treat wound infection and suppuration, and inability to induce regeneration in wounds. Therefore, a product having a superior hemostatic effect and an excellent tissue repairing effect is one of the clinical products urgently needed in the field of surgery.

CN101890179A provides a water-soluble hemostatic material which is mainly composed of oxidized regenerated cellulose ether, has a significant hemostatic effect but insufficient strength, is difficult to degrade in the body, and may be deposited in other organs of the human body after absorption.

CN104558675A provides a hemostatic microfibrous collagen sponge having a good hemostatic effect. However, it is difficult to ensure a controllable structure and quality of the product because only physical thermal cross-linking is applied, and there are also risks posed by immunogenicity and animal viruses.

CN103432620A provides an anti-adhesion hemostatic film mainly composed of dextran and prepared by electrospinning after cross-linking, the production process thereof is relatively complex, the cost is high, and the biocompatibility, which is a strict requirement set upon clinical products, has not been evaluated.

SUMMARY

Due to the defects in the prior art, the first objective of the present disclosure is to provide a recombinant collagen; the second objective of the present disclosure is to provide a recombinant collagen sponge material having a hemostatic and wound surface repairing effect; the third objective of the present disclosure is to provide a method for preparing the recombinant collagen sponge material; and the fourth objective of the present disclosure is to provide use of the recombinant collagen sponge material as a hemostatic product in hemostasis and wound surface repair.

The objectives of the present disclosure are achieved through the following technical solutions.

In one aspect, the present disclosure provides a recombinant collagen, comprising:
(a) a protein composed of the amino acid sequence represented by SEQ ID NO: 2;

```
                                              SEQ ID NO: 2
GPPGEPGNPGKPGSPGPAGSNGEPGPAGSPGEKGSQGSNGNPGPAGNQGQ

PGNKGSPGNPGKPGEPGSNGPQGEPGSQGNPGKNGQPGSPGSQGSPGNQG

QPGKPGQPGEQGSPGNQGPAGNEGPKGQPGQNGKPGSPGPPGEPGNPGKP

GSPGPAGSNGEPGPAGSPGEKGSQGSNGNPGPAGNQGQPGNKGSPGNPGK

PGEPGSNGPQGEPGSQGNPGKNGQPGSPGSQGSPGNQGQPGKPGQPGEQG

SPGNQGPAGNEGPKGQPGQNGKPGTPGPPGEPGNPGKPGSPGPAGSNGEP

GPAGSPGEKGSQGSNGNPGPAGNQGQPGNKGSPGNPGKPGEPGSNGPQGE

PGSQGNPGKNGQPGSPGSQGSPGNQGQPGKPGQPGEQGSPGNQGPAGNEG

PKGQPGQNGKP
```
and/or
(b) a protein which has the same function as (a) and is derived from (a) by substitution, deletion and/or addition of one or more amino acids in SEQ ID NO:2.

Based on the Gly-X-Y repeats of human type I collagen as the smallest repeating unit, the inventors creatively used the hydrophilic Gly-X-Y for permutation and combination, and designed a collagen with a length of 411 amino acids (represented by SEQ ID NO: 2). A corresponding nucleotide sequence (represented by SEQ ID NO: 1) was also designed according to the codon preference in *Pichia*, synthesized, and inserted into the expression vector pPIC9K of *Pichia* to construct a pPIC9K-COL expression vector. The vector was transformed into a *Pichia* host strain GS115 by electrotransformation, high-copy number strains were picked through screening with the antibiotic G418, and finally a high-expression engineered strain of *Pichia* was obtained through shaking flask screening. This engineered strain was subjected to large-scale biological fermentation to obtain the raw material of the recombinant collagen. The recombinant collagen according to the present disclosure shows excellent cell attachment and hydrophilicity, and is an optimal raw material for preparing a recombinant collagen sponge material.

In another aspect, the present disclosure further provides a polynucleotide encoding the amino acid sequence of the recombinant collagen above, and the DNA sequence of the polynucleotide comprises the DNA sequence represented by SEQ ID NO:1.

SEQ ID NO: 1
GGTCCTCCCGGCGAACCAGGTAATCCTGGTAAACCTGGTTCTCCCGGCCC

AGCTGGTTCCAACGGGGAGCCGGGTCCTGCCGGCTCACCCGGAGAAAGG

GGTCGCAAGGTAGTAATGGCAACCCAGGACCGGCAGGGAATCAGGGTCAA

CCTGGCAACAAAGGAAGCCCCGGGAATCCAGGTAAGCCGGGCGAGCCTGG

ATCTAACGGGCCCCAGGGTGAACCAGGCTCCCAAGGAAATCCGGGGAAAA

ACGGTCAGCCTGGCTCACCCGGATCGCAAGGGAGTCCAGGTAATCAGGGC

CAACCGGGAAAGCCTGGGCAGCCCGGTGAGCAAGGCAGCCCAGGAAACCA

GGGGCCGGCGGGTAATGAAGGCCCTAAAGGACAACCCGGGCAGAACGGTA

AGCCAGGATCCCCGGGTCCTCCCGGCGAACCAGGTAATCCTGGTAAACCT

GGTTCTCCCGGCCCAGCTGGTTCCAACGGGGAGCCGGGTCCTGCCGGCTC

ACCCGGAGAAAGGGGTCGCAAGGTAGTAATGGCAACCCAGGACCGGCAG

GGAATCAGGGTCAACCTGGCAACAAAGGAAGCCCCGGGAATCCAGGTAAG

CCGGGCGAGCCTGGATCTAACGGGCCCCAGGGTGAACCAGGCTCCCAAGG

AAATCCGGGGAAAAACGGTCAGCCTGGCTCACCCGGATCGCAAGGGAGTC

CAGGTAATCAGGGCCAACCGGGAAAGCCTGGGCAGCCCGGTGAGCAAGGC

AGCCCAGGAAACCAGGGGCCGGCGGGTAATGAAGGCCCTAAAGGACAACC

CGGGCAGAACGGTAAGCCAGGTACCCCAGGTCCTCCCGGCGAACCAGGTA

ATCCTGGTAAACCTGGTTCTCCCGGCCCAGCTGGTTCCAACGGGGAGCCG

GGTCCTGCCGGCTCACCCGGAGAAAGGGGTCGCAAGGTAGTAATGGCAA

CCCAGGACCGGCAGGGAATCAGGGTCAACCTGGCAACAAAGGAAGCCCCG

GGAATCCAGGTAAGCCGGGCGAGCCTGGATCTAACGGGCCCCAGGGTGAA

CCAGGCTCCCAAGGAAATCCGGGGAAAAACGGTCAGCCTGGCTCACCCGG

ATCGCAAGGGAGTCCAGGTAATCAGGGCCAACCGGGAAAGCCTGGGCAGC

CCGGTGAGCAAGGCAGCCCAGGAAACCAGGGGCCGGCGGGTAATGAAGGC

CCTAAAGGACAACCCGGGCAGAACGGTAAGCCA

In yet another aspect, the present disclosure further provides an expression vector containing the above-mentioned polynucleotide.

In yet another aspect, the present disclosure further provides a host strain containing the above polynucleotide, the host strain being an engineered *Pichia* strain that has been deposited (Date of deposit: Jan. 8, 2020; Depository authority: China General Microbiological Culture Collection Center (CGMCC); Address of depository authority: Institute of Microbiology Chinese Academy of Sciences, Building 3, No. 1 West Beichen Road, Chaoyang District, Beijing; Accession number: CGMCC No. 19314; Taxonomic name: *Pichia* sp.). The recombinant collagen according to the present disclosure is obtained by fermentation of the engineered *Pichia* strain.

In a further aspect, the present disclosure also provides a recombinant collagen sponge material, obtained by sequential physical cross-linking and chemical cross-linking of the aforementioned recombinant collagen; wherein the recombinant collagen sponge material has a moisture absorption capacity of 40-50, and porosity of 90% or higher.

In the present disclosure, the moisture absorption capacity refers to the ratio of the weight of the recombinant collagen sponge material after water absorption to the weight of the recombinant collagen sponge material before water absorption. Porosity refers to the percentage of the pore volume in the recombinant collagen sponge material to the total volume of the recombinant collagen sponge material in its natural state.

The present disclosure achieves high porosity by low-degree cross-linking and freeze-drying techniques, as low-degree cross-linking (10%-20%) can ensure a good swelling property of the product, and freeze-drying can ensure uniform and stable pore distribution. The high water absorption according to the present disclosure is mainly determined by the designed amino acid sequence of the recombinant protein and the interconnected high porosity. Specifically, the designed amino acids increased the number of hydrophilic amino acids to improve water absorption, and the interconnected high porosity can provide water absorption and water retention.

In yet another aspect, the present disclosure provides a method for preparing the above-mentioned recombinant collagen sponge material, comprising the following steps:
dissolving the aforementioned recombinant collagen in water to obtain a recombinant collagen solution;
lyophilizing the recombinant collagen solution by a freeze-drying method; and
subjecting the lyophilized and formed recombinant collagen to physical cross-linking and chemical cross-linking in sequence to obtain a recombinant collagen sponge material.

The recombinant collagen raw material according to the present disclosure is water-soluble, has excellent cell attachment property and hydrophilicity, has a low crosslinking degree after the physical crosslinking and chemical cross-linking to ensure the mechanical strength of the sponge while avoiding a risk of inflammation caused by prolonged retention of residual material in the body. After the low-degree cross-linking and freeze-drying process, a collagen sponge with good water absorption is obtained. The special amino acid sequence design improves the attachment of platelets, while the high water absorption can concentrate the platelets in the blood to rapidly stop bleeding.

Generally, by physical crosslinking alone it is difficult to obtain a uniform degree of crosslinking and the quality is uncontrollable, while chemical crosslinking alone often requires involvement of a high level of chemical crosslinking agents, which affects the biocompatibility of the final product. The present disclosure adopts the "physical plus chemical" cross-linking and can obtain a recombinant collagen sponge material having a low cross-linking degree and excellent biocompatibility.

In the above method, preferably, the recombinant collagen sponge material obtained after the cross-linkings is further subjected to washing, drying, and sterilization.

In the above method, preferably, the device used for the washing includes a rotating rod and a porous clamp box fixed on the rotating rod; wherein the porous clamp box is used to hold the recombined collagen sponge, and the rotating rod is used to rotate and drive the porous clamp box to flip in a cleaning medium, so as to wash off the residual reagent in the recombinant collagen sponge material.

The washing device according to the present disclosure is an independently designed device, wherein the designed porous clamp box has an effect of fixing and shaping the recombined sponge, and the rotation of the rotating rod drives the clamp box to flip in a cleaning medium, which can improve the efficiency of washing off residual reagents in the recombined sponge. Due to the high efficiency of the washing device and the use of low-degree crosslinking agents, the biocompatibility of the product is ensured.

In the above method, preferably, the drying includes one or a combination of more of oven drying, freeze drying and vacuum drying.

In the above method, preferably, the sterilization is performed by 15 to 25 kGy $Co^{60}$ irradiation.

In the above method, preferably, the physical crosslinking includes one or a combination of more of thermal crosslinking, radiation crosslinking, and repeated freezing-reconstitution.

In the above method, preferably, the temperature for thermal crosslinking is 110° C., and the crosslinking duration is 2 h.

In the above method, preferably, the radiation source for the radiation cross-linking includes ultraviolet rays and/or gamma rays.

In the above method, preferably, the chemical crosslinking is performed by addition of a chemical crosslinking agent including one or a combination of more of glutaraldehyde, carbodiimide, and genipin.

In the above method, preferably, the concentration of the chemical crosslinking agent is 0.005 to 0.015 mol/L.

In the above method, preferably, the mass ratio of the chemical crosslinking agent to the recombinant collagen is 1:1 to 5.

After cross-linking, the recombinant collagen sponge material according to the present disclosure has a low degree of cross-linking of 10%-20%, as determined by percentage analysis of free amino groups on the side chains of amino acids.

In the above method, preferably, the chemical crosslinking duration is 1 to 5 hours.

In the above method, preferably, the concentration of the recombinant collagen solution is 1% to 5%.

In the above method, preferably, before freeze-drying the recombinant collagen solution, it further includes injecting the recombinant collagen solution into a mold for forming.

In the above method, preferably, the recombinant collagen solution is freeze-dried at a gradient from −50° C. to 30° C.

In another aspect, the present disclosure further provides use of the above-mentioned recombinant collagen sponge material as a hemostatic product in hemostasis and wound surface repair. It is mainly applicable in the field of medical surgery, for hemostasis of acute and chronic wounds during surgeries and tissue repair at wound surfaces.

The recombinant collagen raw material according to the present disclosure is water-soluble, shows excellent cell attachment property and hydrophilicity, and provides a collagen sponge having good water absorption after being subjected to low-degree cross-linking and freeze-drying processes. The high efficiency of the washing device and use of a low-degree crosslinking agent ensure the biocompatibility of the product. The special amino acid sequence design improves the platelet attachment ability, and the high water absorption can concentrate the platelets in the blood so as to quickly stop bleeding. In summary, the recombinant collagen sponge material according to the present disclosure is capable of hemostasis, wound surface repair, moisture absorption and platelet aggregation, and has high moisture absorption, a significant hemostatic effect and good biocompatibility, assuming great clinical significance in the field of surgery.

DEPOSITION OF MICROORGANISMS FOR THE PURPOSE OF PATENT PROCEDURES

The engineered *Pichia* strain according to the present disclosure:
Date of deposit: Jan. 8, 2020;
Depository authority: China General Microbiological Culture Collection Center (CGMCC);
Address of depository authority: Building 3, No. 1 West Beichen Road, Chaoyang District, Beijing;
Accession number: CGMCC No. 19314;
Taxonomic name: *Pichia* sp.

DETAILED DESCRIPTION OF INVENTION

In order to provide a clearer understanding of the technical features, objectives and beneficial effects of the present disclosure, the technical solutions of the present disclosure will be described in detail below, but are not to be construed as limiting the implementable scope of the present disclosure.

The recombinant collagen raw material used in the following examples was obtained by constructing a genetically engineered strain, producing a recombinant collagen having a molecular weight of 38 kDa by microbial fermentation, purifying and then freeze-drying the recombinant collagen.

The specific process was as follows.

Figure 1:
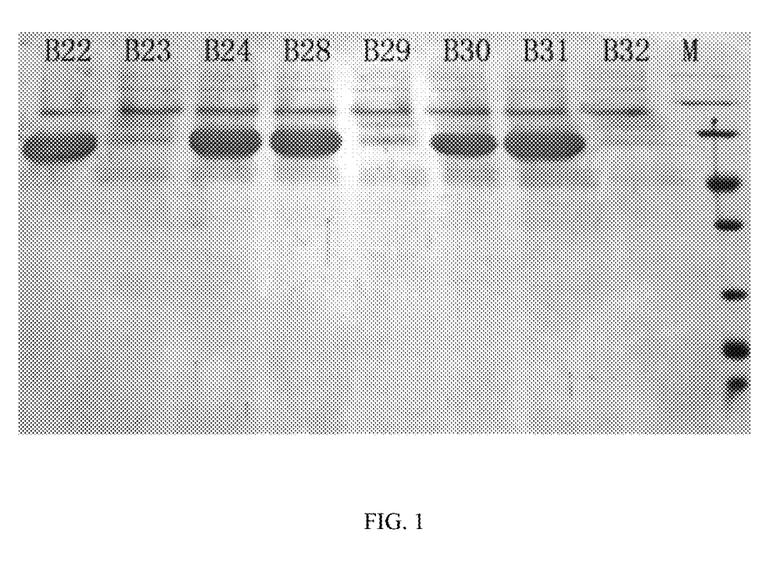
FIG. 1 shows the results of an electrophoresis of protein expression levels in different strains according to the present disclosure. B22-B24 and B28-B32 in FIG. 1 are strains obtained during the strain screening process according to the invention. M is a molecular weight marker used in electrophoresis.

Based on the Gly-X-Y repeats of human type I collagen as the smallest repeating unit, the inventors creatively used the hydrophilic Gly-X-Y for permutation and combination, and designed a collagen with a length of 411 amino acids (represented by SEQ ID NO: 2). A corresponding nucleotide sequence according to the codon preference in *Pichia* (represented by SEQ ID NO:1) was also designed, synthesized, and inserted into the expression vector pPIC9K of *Pichia* to construct a pPIC9K-COL expression vector. The vector was transformed into a *Pichia* host strain GS115 by electrotransformation, high-copy number strains were picked through screening with increasing concentrations of Geneticin G418 in the medium, transformants with a high copy number were picked for an expression test in shaking flasks, and strains showing a high level of expression were selected as the genetically engineered strain for production. Under the same electrophoresis conditions, the strain B31 showed a relatively high expression level (as shown in FIG. 1), and was deposited as an engineered strain (accession number: CGMCC No. 19314) for scale-up production. The engineered strain was used to carry out large-scale biological fermentation to obtain the raw material of the recombinant collagen.

The process of obtaining the recombinant collagen by fermenting the engineered strain according to the present disclosure was as follows.

(1) Primary Seed Cultivation

The engineered strain of the present disclosure (Accession number: CGMCC No. 19314) was inoculated into an Erlenmeyer flask containing a BMGY medium, and incubated in a thermostatic culturing shaker at 29° C., 225 rpm for 60 to 70 hours to obtain a primary seed liquid.

(2) Secondary Seed Cultivation

The primary seed liquid was fed into a seed tank, and then cultured in the tank at a temperature controlled at 29.0±1.0° C., a tank pressure of 0.050±0.010 MPa, and pH 5.0. During the culturing, the aeration and stirring speed were adjusted to maintain the dissolved oxygen at about 30%. The secondary seed cultivation was performed for about 16 hours to obtain a secondary seed liquid.

(3) Fermentation in Fermenter

Base Material Cultivation Stage

After the secondary seed cultivation was complete, the secondary seed liquid was transferred to a fermenter, the culturing temperature was controlled at 29.0±1.0° C., the tank pressure was controlled at 0.050±0.010 MPa, and the DO was controlled at about 30% by manual adjustment of the aeration, oxygen level and rotation speed. After 12 to 18 hours of cultivation, the feeding cultivation stage started.

Glycerin Feeding Stage

When the feeding stage started, the oxygen supply was immediately turned off, and the DO was lowered to about 40% by reducing the stirring speed. An automatic feeding system was started with an initial flow rate of a glycerin solution of 0.8 mL/min (1 s/60 s). After 12 hours of feeding, a sample was taken to measure the wet strain weight of the fermentation broth. When the wet strain weight of the fermentation broth reached 200 g/L, the glycerin feeding was stopped and starvation was started.

Starvation Stage

The DO was controlled at 30-40% by adjusting the aeration volume and reducing the stirring speed, and the starvation state was maintained for 1.0 h.

Methanol Induction Stage

The methanol flow rate was increased according to the actual DO. The methanol flow rate was generally controlled within 8.0 mL/min (10 s/60 s), and the methanol induction duration was generally controlled at 40 to 48 h. The DO during methanol induction should be controlled at 20 to 35%, and it should be confirmed that no excessive methanol was accumulated at this stage.

Discharge from Fermenter

After induction for 44 to 48 hours, the recombinant collagen was discharged from the fermenter, harvested, and sampled for testing.

The amino acid sequence of the recombinant collagen is represented by SEQ ID NO: 2:

```
                                          SEQ ID NO: 2
GPPGEPGNPGKPGSPGPAGSNGEPGPAGSPGEKGSQGSNGNPGPAGNQGQ

PGNKGSPGNPGKPGEPGSNGPQGEPGSQGNPGKNGQPGSPGSQGSPGNQG

QPGKPGQPGEQGSPGNQGPAGNEGPKGQPGQNGKPGSPGPPGEPGNPGKP

GSPGPAGSNGEPGPAGSPGEKGSQGSNGNPGPAGNQGQPGNKGSPGNPGK

PGEPGSNGPQGEPGSQGNPGKNGQPGSPGSQGSPGNQGQPGKPGQPGEQG

SPGNQGPAGNEGPKGQPGQNGKPGTPGPPGEPGNPGKPGSPGPAGSNGEP

GPAGSPGEKGSQGSNGNPGPAGNQGQPGNKGSPGNPGKPGEPGSNGPQGE

PGSQGNPGKNGQPGSPGSQGSPGNQGQPGKPGQPGEQGSPGNQGPAGNEG

PKGQPGQNGK
```

The recombinant collagen according to the present disclosure shows excellent cell attachment property and hydrophilicity, and is an optimal raw material for preparing a recombinant collagen sponge material.

Figure 2:
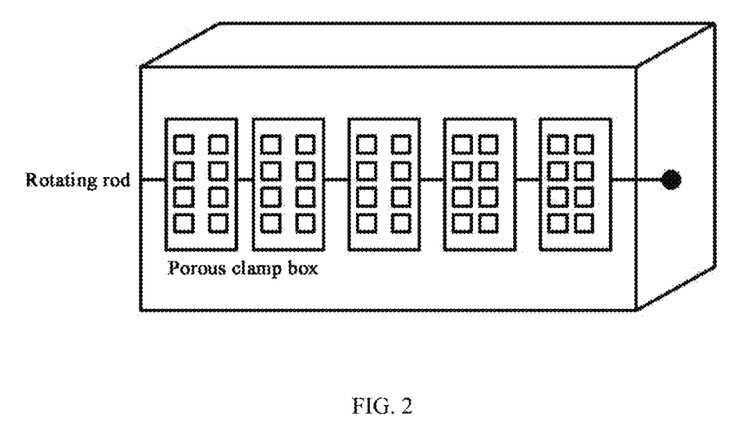
FIG. 2 is a schematic representation of the structure of the washing device used in an example of the present disclosure.

The washing device used in the following Examples was shown in FIG. 2. The washing device includes a rotating rod and a porous clamp box fixed on the rotating rod; wherein the porous clamp box is used to hold the recombined collagen sponge, and the rotating rod is used to rotate and drive the porous clamp box to flip in a cleaning medium, so as to wash off residual reagents in the recombinant collagen sponge material.

Example 1

This Example provides a recombinant collagen sponge material and a method for preparation thereof. The method comprised:
(1) preparing a 3% solution of a recombinant collagen (molecular weight: 38 kDa) and stirring it thoroughly; pouring the recombinant collagen solution into a mold for forming, and lyophilizing it by a freeze-drying method with the following lyophilization parameters: −50° C. for 5 h, −30° C. for 3 h, −20° C. for 3 h, −10° C. for 2 h, 0° C. for 1 h, 10° C. for 5 h, 20° C. for 20 h, 30° C. for 60 h;
(2) performing physical crosslinking with ultraviolet radiation at a radiation distance of 20 cm for 6 h, and then performing chemical crosslinking with 0.01 mol/L carbodiimide (the mass ratio of carbodiimide to recombinant collagen was 1:1) at a reaction temperature of 4° C. for 5 h;
(3) washing in the washing device according to the present disclosure 5 times, with 20 minutes each time;
(4) drying the washed recombinant collagen sponge at a temperature of 60° C. for 3 hours; encapsulating a sample thereof and sterilizing it with 15 kGy $Co^{60}$ irradiation to obtain a recombinant collagen sponge material.

Example 2

This Example provides a recombinant collagen sponge material and a method for preparation thereof. The method comprised:
(1) preparing a 5% solution of a recombinant collagen (molecular weight: 38 kDa) and stirring it thoroughly; pouring the recombinant collagen solution into a mold for forming, and lyophilizing it by a freeze-drying method with the following lyophilization parameters:

−50° C. for 6 h, −30° C. for 2 h, −20° C. for 2 h, −10° C. for 2 h, 0° C. for 2 h, 10° C. for 10 h, 20° C. for 20 h, 30° C. for 50 h;
(2) performing physical crosslinking at a high temperature of 110° C. for 2 h, and then performing chemical crosslinking with a 0.005 mol/L solution of genipin (the mass ratio of genipin to recombinant collagen was 1:4) at a reaction temperature of 25° C. for 2 h;
(3) washing in the washing device according to the present disclosure 6 times, with 15 minutes each time;
(4) freeze-drying the washed recombinant collagen sponge with the same lyophilization parameters as in the first washing; encapsulating a sample thereof and sterilizing it with 25 kGy $Co^{60}$ irradiation to obtain a recombinant collagen sponge material.

Example 3

This Example provides a recombinant collagen sponge material and a method for preparation thereof. The method comprised:
(1) preparing a 1% solution of a recombinant collagen (molecular weight: 38 kDa) and stirring it thoroughly; pouring the recombinant collagen solution into a mold for forming, and lyophilizing it by a freeze-drying method with the following lyophilization parameters: −50° C. for 6 h, −30° ° C. for 2 h, −10° C. for 4 h, 0° C. for 2 h, 10° C. for 5 h, 20° C. for 20 h, 30° C. for 50 h;
(2) performing physical crosslinking with y rays at a radiation dose of 35 kGy, and then performing chemical crosslinking with a 0.015 mol/L solution of glutaraldehyde (the mass ratio of glutaraldehyde to recombinant collagen was 1:4) at a reaction temperature of 25° C. for 1 h;
(3) washing in the washing device according to the present disclosure 9 times, with 10 minutes each time;
(4) freeze-drying the washed recombinant collagen sponge with the same lyophilization parameters as in the washing; encapsulating a sample thereof and sterilizing it with 25 kGy $Co^{60}$ irradiation to obtain a recombinant collagen sponge material.

Test Experiments

1. Cell Proliferation Test on Recombinant Collagen Sponge Material

A sample material with an appropriate size (Example 1) was put in a well plate, and L929 cells growing in the exponential phase was inoculated onto the material placed in the well plate at a density of $2\times10^5$ cells. One hour later, 1 ml medium was supplemented to each well and the culturing was continued. After 20 hours, the material was gently rinsed with PBS 3 times and transferred into a new well, and the cell quantity was measured by a CCK-8 method. 1 ml of a medium containing 10% (volume fraction) CCK-8 reagent was added to each well. After incubation for 2 h in an incubator, the absorbance at 450 nm was measured with a microplate reader. In the proliferation test, after the cells were inoculated and cultured for 1 d, 3 d, 5 d, and 7 d, the number of cells was measured by the CCK-8 method, and the growth of the cells in the material was observed. The experimental results are shown in FIG. 3.

Figure 3:
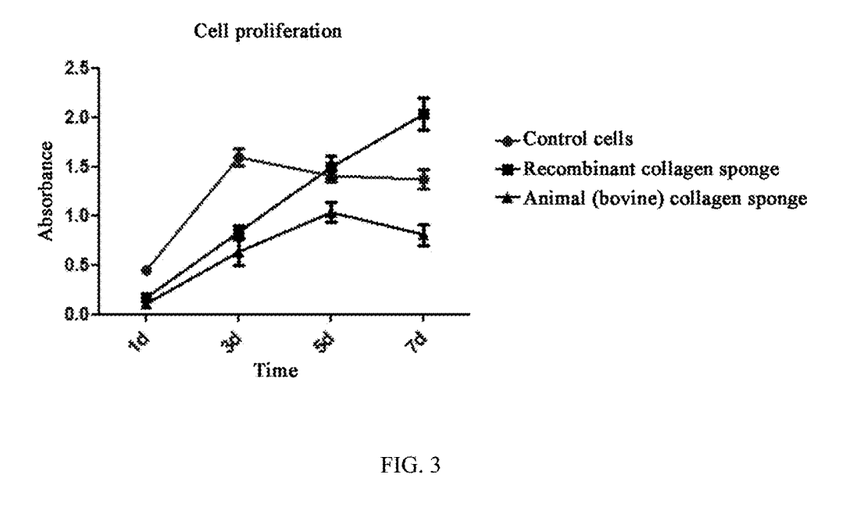
FIG. 3 shows a comparative experiment of cell proliferation in the recombinant collagen sponge material in an example of the present disclosure.

It can be seen from FIG. 3 that the cell quantity in the blank control group began to decrease after 3 days, and the cell quantity in the bovine collagen sponge control group began to decrease after 5 days. The test group showed an increasing trend from 1 to 7 days, indicating that the recombinant collagen sponge material can provide a more effective space and growth environment for cell proliferation, and has a good effect of guiding tissue repair.

2. Water Absorption Performance Test on Recombinant Collagen Sponge Material

The weight of the sample (Example 2) was measured as m1, and the weight after sufficient water absorption in physiological saline (10 s) was recorded as m2. According to the equation: Water absorption rate=(m2-m1)/m1, the water absorption rate of each sample was calculated. The results are shown in Table 1 below which shows a comparison of the water absorption rate between samples in two groups.

TABLE 1

| Group | Water absorption rate |
| --- | --- |
| Control (Bovine collagen sponge) | 22.6 ± 2.1 |
| Test (The recombinant collagen sponge of Example 2) | 44.3 ± 5.8* |

It can be seen from Table 1 that the moisture absorption rate of the test group was significantly higher than that of the control group, and the difference was statistically significant (P<0.05).

3. Hemostatic Performance Test on Recombinant Collagen Sponge Material

The evaluation was carried out by the liver hemostasis test in New Zealand rabbits. Specifically, a New Zealand rabbit was laparotomized layer by layer and the liver was exposed. A 0.5 cm*1.0 cm bleeding wound was made on the liver lobe of the rabbit with a razor blade. The bleeding site was immediately subjected to hemostatic treatment with the recombinant collagen sponge or a natural collagen sponge, and the hemostatic effect and duration for local hemostasis were observed. After observation for a certain period of time, the hemostatic material was removed to observe whether the bleeding continued. The experimental results are shown in FIG. 4.

Figure 4:
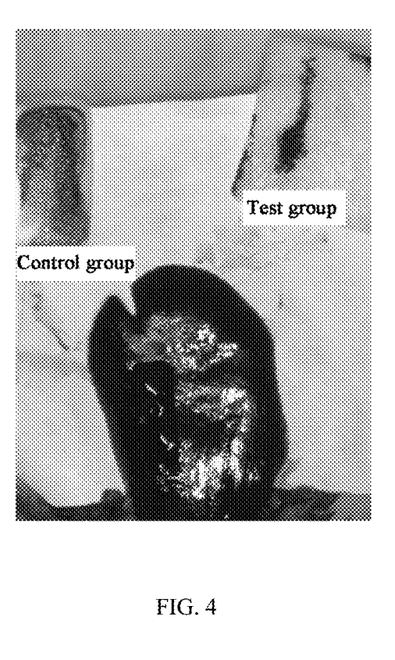
FIG. 4 shows a comparative experiment of hemostatic performance of the recombinant collagen sponge material on a New Zealand rabbit liver over 20 seconds in an example of the present disclosure.

It can be seen from FIG. 4 that, as observed after 20 s hemostatic treatment with the control group (bovine collagen sponge) and the test group (recombinant collagen sponge) and removal of the material, the test group completely stopped bleeding, while the control group still showed bleeding and did not complete the hemostasis.

It can be known from the above measurement and evaluation results that the recombinant collagen sponge material prepared according to the present disclosure has good clinical effectiveness and can be applied to hemostasis and wound repair in the field of medical surgeries.

Figure 5:
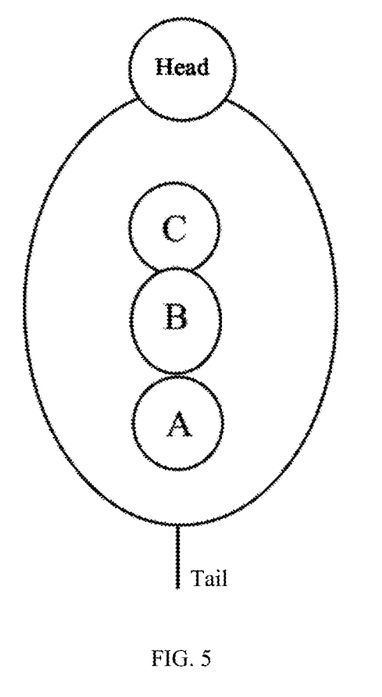
FIG. 5 is a schematic representation of a wound surface model on the back of a rat in an example of the present disclosure, where group A is a recombinant collagen sponge material group, group B is a control group, and group C is a blank group.

4. Wound Surface Repair Test on Recombinant Collagen Sponge Material (1) Rats were allowed to adapt to the environment for one week after purchased to the laboratory.
(2) The rats were anesthetized and subjected to skin preparation, where intraperitoneal anesthetization was performed with 3% sodium pentobarbital at an anesthetic dose of 30 mg/kg, and after successful anesthesia, the back was shaved with an electric clipper.
(3) Three round full-thickness skin excision wounds having a diameter of 15 mm and an area of 1.766 $cm^2$ were created on the back of the animals with a modelling skin sampler (diameter 15 mm), and marked with Indian ink. The wounds were A, B, C, respectively corresponding to the group of the recombinant collagen sponge material of Example 1 (i.e., Material group A), the bovine collagen group (i.e., Control group B), and the blank control group (i.e., Blank group C). After the model was established, the wound was covered with the corresponding sponge and fixed with transparent waterproof medical tape (as shown in FIG. 5).

Figure 6:
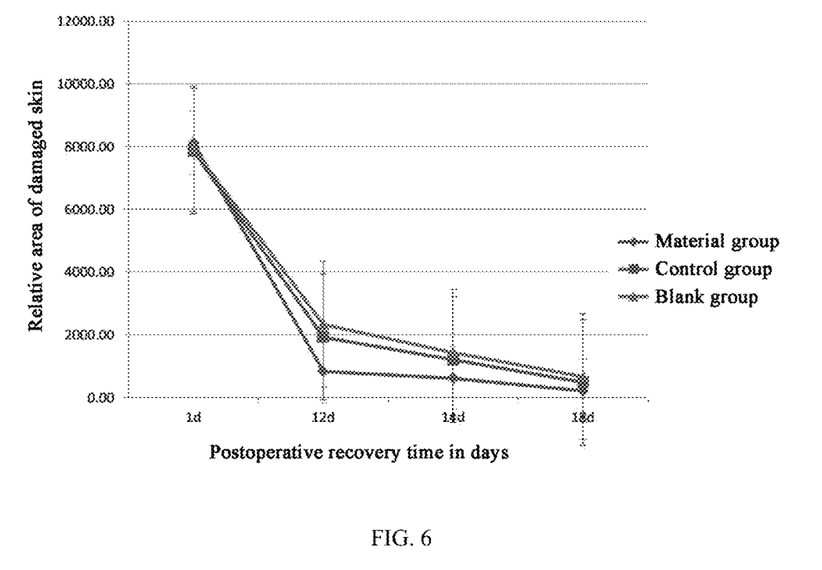
FIG. 6 shows the repairing of wound surfaces with the materials in various groups at different time points in an example of the present disclosure.

The wound surface repairing was observed for 3 to 18 days after the surgery, and the results are shown in FIG. 6 (the ordinate represents the relative value of the area of damaged skin, and the abscissa represents the postoperative recovery time). It can be seen from FIG. 6 that the wound surfaces in the three groups were all repaired and shrunk over time, wherein the recombinant collagen sponge material group was significantly better than the control group and the blank group, with statistical significance ($P<0.05$).

5. Validation Experiment on Recombinant Collagen Raw Material

The engineered *Pichia* strain according to the present disclosure was used to carry out large-scale biological fermentation to obtain the recombinant collagen raw material, and the sequence and molecular weight of the raw material protein were determined by N-terminal sequencing, amino acid analysis and mass spectrometry. The results are as follows.

1) N-Terminal Sequencing

The N-terminal sequence of the sample was determined by Edman degradation as: NH2-Gly-Pro-Pro-Gly-Glu-Pro-Gly-Asn-Pro-Gly-Lys-Pro-Gly-Ser-Pro (shown in SEQ ID NO: 3), which is consistent with the designed sequence.

2) Amino Acid Analysis

Figure 7:
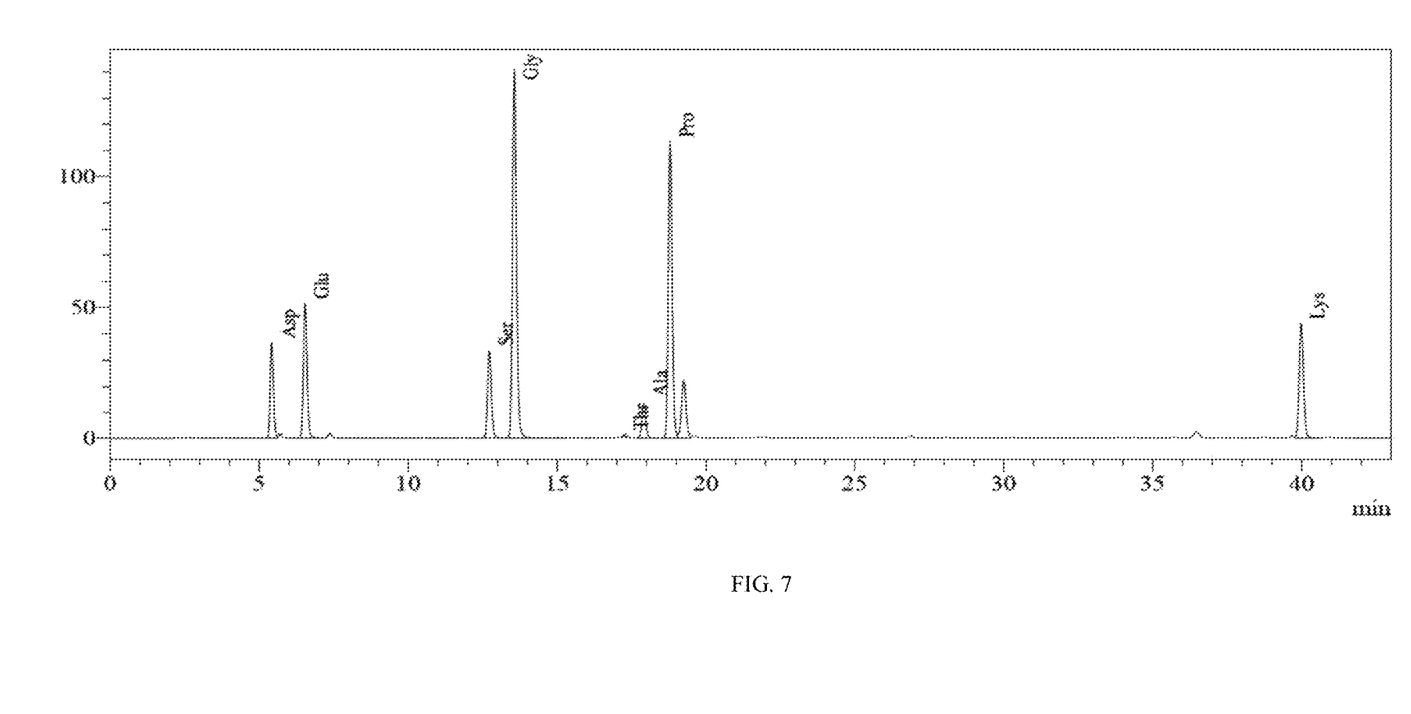
FIG. 7 shows a liquid chromatography profile for a compositional analysis of the amino acid components of the recombinant collagen in an example of the present disclosure.

It can be seen from FIG. 7 that the amino acid composition of the prepared sample was G, E, S, T, A, P, K, N, which are consistent with the designed amino acid composition.

3) Mass Spectroscopy

Figure 8:
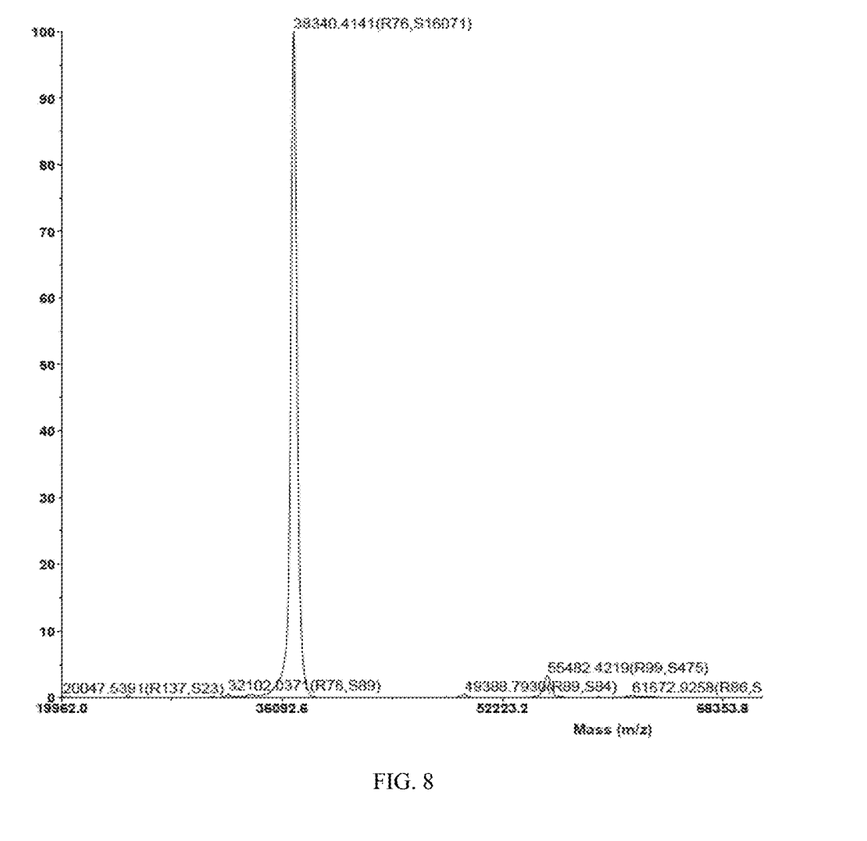
FIG. 8 is a mass spectrometry profile of the molecular weight of the recombinant collagen in an example of the present disclosure.

It can be seen from the mass spectrometry profile in FIG. 8 that the molecular weight of the sample was about 38 kDa, which is consistent with the designed value.

Conclusion: The prepared recombinant collagen is consistent with the designed requirements and is a 38 kDa recombinant collagen.

---

What is claimed is:

1. An engineered *Pichia* GS115 strain deposited with Accession No. CGMCC 19314, wherein a recombinant collagen is produced by fermentation of the strain, and wherein the recombinant collagen comprises the amino acid sequence of SEQ ID NO: 2.

2. A recombinant collagen sponge material, obtained by a process comprising sequential physical cross-linking and chemical cross-linking of a recombinant collagen comprising the amino acid sequence of SEQ ID NO: 2,
wherein the recombinant collagen sponge material has a moisture absorption capacity of 40-50 weight percent (wt %), and a porosity of 90% or higher, and
wherein the moisture absorption capacity is the ratio of the weight of the recombinant collagen sponge material after water absorption to the weight of the recombinant collagen sponge material before the water absorption.

3. A method for preparing the recombinant collagen sponge material of claim 2, comprising:
dissolving the recombinant collagen comprising the amino acid sequence of SEQ ID NO: 2 in water to obtain a recombinant collagen solution;
lyophilizing the recombinant collagen solution by a freeze-drying method; and
subjecting the lyophilized and formed recombinant collagen to physical cross-linking and chemical cross-linking in sequence, to obtain the recombinant collagen sponge material.

4. The method of claim 3, wherein the recombinant collagen sponge material obtained after the cross-linkings is further subjected to washing, drying, and sterilization.

5. The method of claim 4, wherein the device used for the washing comprises a rotating rod and a porous clamp box fixed on the rotating rod; and wherein the porous clamp box is used to hold the recombined collagen sponge material, and the rotating rod is used to rotate and drive the porous clamp box to flip in a cleaning medium, so as to wash off residual reagents in the recombinant collagen sponge material.

6. The method of claim 4, wherein the drying comprises includes one or more of oven drying, freeze drying, and vacuum drying.

7. The method of claim 4, wherein the sterilization is performed by 15 to 25 kGy $Co^{60}$ irradiation.

8. The method of claim 3, wherein the physical cross-linking comprises one or more of thermal cross-linking, radiation cross-linking, and repeated freezing-reconstitution.

9. The method of claim 8, wherein the temperature for the thermal cross-linking is 110° C., and the cross-linking duration is 2 hours.

10. The method of claim 3, wherein the chemical cross-linking is performed by addition of a chemical cross-linking agent comprising one or more of glutaraldehyde, carbodiimide, and genipin.

11. The method of claim 3, wherein the concentration of a chemical cross-linking agent is 0.005 to 0.015 mol/L.

12. The method of claim 3, wherein the concentration of the recombinant collagen solution is 1% to 5% w/v.

13. The method of claim 3, further comprising injecting the recombinant collagen solution into a mold for forming before the recombinant collagen solution is subjected to freeze-drying.

14. The method of claim 8, wherein the radiation source for the radiation cross-linking comprises ultraviolet rays and/or gamma rays.

15. The method of claim 11, wherein a mass ratio of the chemical cross-linking agent to the recombinant collagen is 1:1 to 5.

16. The method of claim 11, wherein the chemical cross-linking duration is 1 to 5 hours.

17. The method of claim 13, wherein the recombinant collagen solution is freeze-dried at a gradient from −50° C. to 30° C.

* * * * *